United States Patent [19]

Lee

[11] Patent Number: 5,173,263

[45] Date of Patent: Dec. 22, 1992

[54] REGENERABLE ACTIVATED BAUXITE ADSORBENT ALKALI MONITOR PROBE

[75] Inventor: Sheldon H. D. Lee, Willowbrook, Ill.

[73] Assignee: The United States of America as represented by the United States Department of Energy, Washington, D.C.

[21] Appl. No.: 643,318

[22] Filed: Jan. 22, 1991

[51] Int. Cl.$^5$ .................. G01N 30/48; G01N 33/20; G01N 30/60; B01D 53/04

[52] U.S. Cl. .................................. 422/88; 422/92; 436/73; 436/79; 55/72; 55/387; 502/407; 502/411

[58] Field of Search ............. 422/88, 92; 436/73, 436/79, 178; 55/72, 387, 270; 502/401, 407, 408, 411

[56] References Cited

U.S. PATENT DOCUMENTS

| | | | |
|---|---|---|---|
| 2,434,389 | 1/1948 | Breth et al. | 502/407 |
| 4,133,762 | 1/1979 | Visceglia et al. | 55/387 X |
| 4,340,399 | 7/1982 | Luthra et al. | 55/72 |
| 4,509,727 | 4/1985 | Davis et al. | 55/270 X |
| 4,636,227 | 1/1987 | Yin et al. | 422/88 X |
| 4,803,051 | 2/1989 | Knapp | 436/73 X |

OTHER PUBLICATIONS

Petrick M.; Stemdler, M. J.; Lee, S. H. D.; Myles, K. M.; Haas, W. J.; Eckels, D. E. "Measurement of Alkali Vapors in PFBC Flue Gas and Their Removal With A Fixed Granular Bed Sorber." *Morgantown Energy Technol. Cent., DOE/METC* 1986, DOE/METC—86/6042, 58–77.

Lee, S. H. D.; Henry, R. F.; Wilson, W. I.; Myles, K. M.; Haas; W. J.; Eckels, D. E. "Measurement of Alkali Vapors in PFBC Flue Gas and Their Control by a Granular-Bed Sorber." *Morgantown Energy Technol. Cent.*, 1986, DOE/METC 85/6025, 513–28.

Lee, S. H. D.; Johnson I., "Alkali Emission and Fixation During Combustion of Coals at the Normal Temperature Range of PFBCs," *Proc. Intersoc. Energy Convers. Eng. Conf.*, 1979, 14th (vol. 1) 942–948.

Lee, S. H. D.; Johnson, I. "Removal of Gaseous Alkali Metal Compounds from Hot Flue Gas by Particulate Sorbents", *J. Engineering Power, 1980*, 102, 397–402.

Lee, S. H. D.; Myles, K. M. "Measurement of Alkali Vapor in PFBC Flue Gas and its Control by a Fixed Granular Bed of Activated Bauxite " *Inst. Chem. Eng. Symp. Ser.* 1986, 99, 149–66.

Lee, S. H. D.; Smith, S. D.; Swift, W. M.; Johnson, I. "Studies of the Regeneration of Activated Bauxite Used as Granular Sorbent for the Control of Alkali Vapors from Hot Flue Gas of Coal Combustion", 1981, Argonne National Laboratory Report ANL/CEN/FE-8-1-1, May.

Lee, S. H. D.; Swift, W. M.; Johnson, I. "Activated Bauxite and Diatomaceous Earth Used as Granular Sorbents for the Removal of Alkali Vapors from Simulated Hot Flue Gas of PFBCs", *Proc. Int. Conf. Fluid. Bed Combust.* 1980, 6th(2), 254–63.

*Primary Examiner*—James C. Housel
*Assistant Examiner*—Arlen Soderquist
*Attorney, Agent, or Firm*—Tyrone Davis; Thomas G. Anderson; William R. Moser

[57] ABSTRACT

A regenerable activated bauxite adsorber alkali monitor probe for field applications to provide reliable measurement of alkali-vapor concentration in combustion gas with special emphasis on pressurized fluidized-bed combustion (PFBC) off-gas. More particularly, the invention relates to the development of a easily regenerable bauxite adsorbent for use in a method to accurately determine the alkali-vapor content of PFBC exhaust gases.

14 Claims, 3 Drawing Sheets

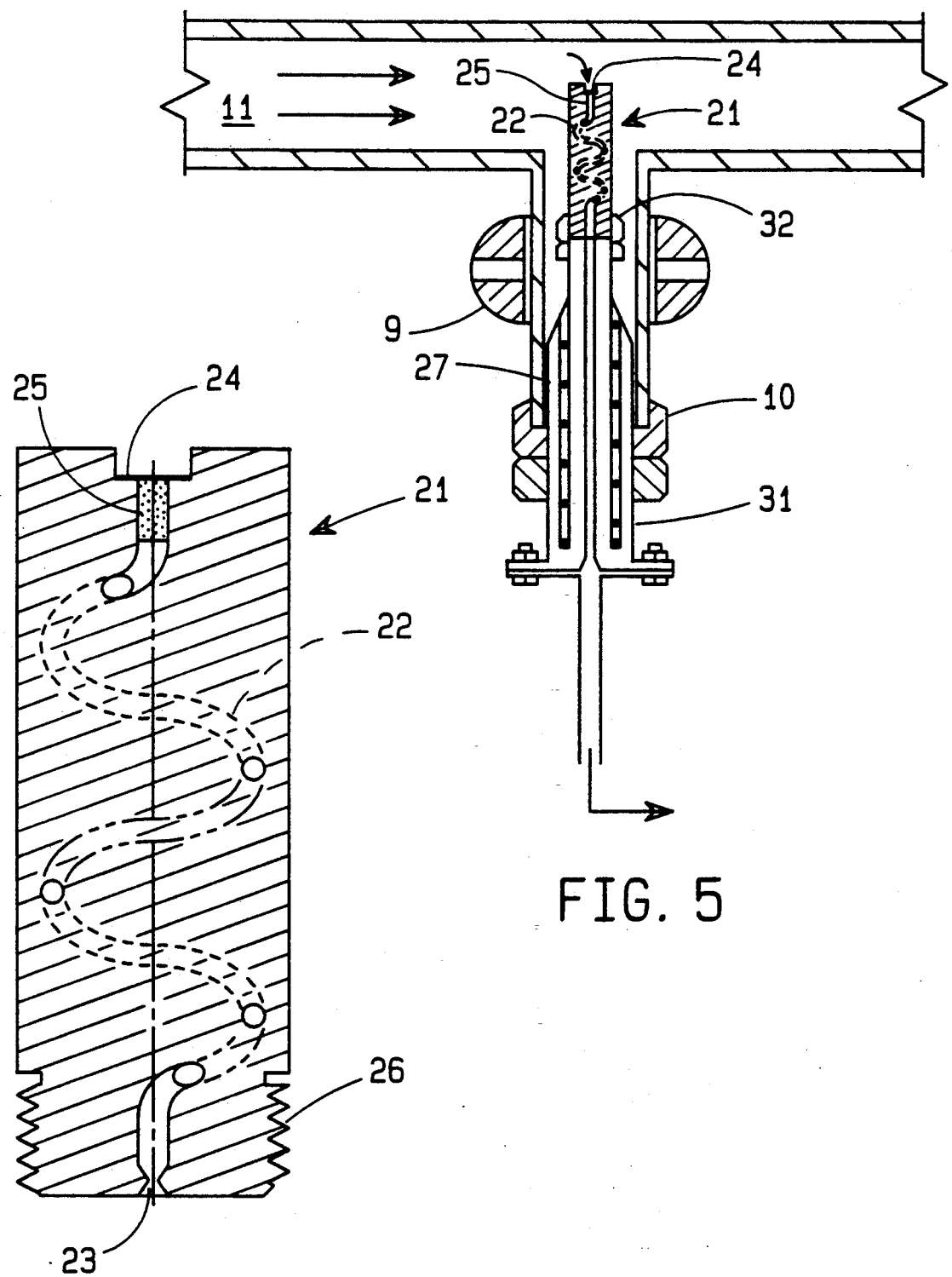

REGENERABLE ACTIVATED BAUXITE ADSORBENT ALKALI MONITOR PROBE

CONTRACTUAL ORIGIN OF THE INVENTION

The United States Government has rights in this invention pursuant to Contract No. W-31-109-ENG-38 between the United States Department of Energy and the University of Chicago.

BACKGROUND OF THE INVENTION

This invention relates to a regenerable activated bauxite adsorbent alkali monitor probe for field applications to provide reliable measurement of alkali-vapor concentration in combustion gas with special emphasis on pressurized fluidized-bed combustion (PFBC) off-gas. More particularly, the invention relates to the development of a easily regenerable bauxite adsorbent for use in a method to accurately determine the alkali-vapor content of PFBC off-gases and the construction of a probe with particular emphasis being directed to a coil-like construction that allows the regenerable activated bauxite to be inserted directly into the PFBC exhaust duct.

Pressurized fluidized bed combustion techniques are under development by Argonne National laboratory and other organizations for the combustion of coal and other fuels at high pressure to produce a gas stream for use in gas turbines. Alkali vapor is usually produced in the combustion and gasification processes for coal and if not removed prior to being fed to the turbine can cause harmful effects in the turbine Thus, it is important that alkali-vapor concentration in the PFBC off-gas be reliably monitored to avoid hot corrosion of turbine hardware. The typical continuous alkali analyzer currently in use requires a lengthy stainless steel sampling line that has been demonstrated to react with alkali vapor and significantly interfere with the accuracy in the measurement of the alkali vapor of the exhaust gases. The present invention provides for a regenerable activated bauxite adsorber alkali monitor to be employed as an alternative to the on-line alkali analyzer, and the development of a regenerable activated bauxite for use as an adsorbent.

SUMMARY OF THE INVENTION

In the invention, a probe is constructed with an inner column containing regenerable bauxite adsorbent exposed to the PFBC off-gas. During the sampling process, the pressurized flow rate of the off-gas is determined and alkali vapor is physically adsorbed on the regenerable activated bauxite adsorbent. The probe is then removed and the adsorbent is water-leached. The leachate is then analyzed for alkalis by atomic absorption spectrometer. Thereafter, the bauxite is regenerated and the probe is reinserted in the exhaust line. The probe is particularly useful for sampling alkali vapor at high temperatures and high pressures, in PFBC off-gas and is useful for the coal gasification/combined-cycle and the MHD system. With respect to the coal gasification it may be required to provide an on-line afterburner to consume the fuel present in the exhaust gases. The sampling length of the adsorbent is determined by the sampling time and break-through point of the alkali vapors through the regenerable activated bauxite adsorbent. The pressurized system requires that all alkali vapors be removed so that the monitoring equipment can accurately determine the flow rates of the exhaust gases. The break through point is dependent upon the sampling time at any given period. The probe can be modified to form a coil in order to minimize the longitudinal length of the probe.

In addition, an activated bauxite adsorbent has been developed to avoid inaccuracies in sample measurements during the first sampling stages apparently caused by impurities in activated bauxite. In developing the regenerable activated bauxite adsorbent the commercially available bauxite product of Engelhard Corporation, N.J., was used. It contains 10 wt% $SiO_2$, 81.5 wt% $Al_2O_3$, and clay impurities. The clay impurities in bauxite has been proven to react with the alkali vapors to cause a chemical fixation and form water-insoluble alkali alumino-silicates (such as, $Na_2O\ Al_2O_3\ 2SiO_2 + HCl$). In order to produce the regenerative activated bauxite adsorbent the clay impurities have to be removed or deactivated so that only a purely physical adsorption occurs (forming $Na_2SO_4 + 2HCl$ molecules). Acid leaching of the activated bauxite is one of the possible ways to remove the clay impurities. However, this process is time consuming and costly to achieve the complete removal of the clay impurities. A technique was developed for the deactivation of the clay impurities, which involves heat treating activated bauxite that was impregnated with NaCl solution. Impregnation occurs when a chemical compound, such as NaCl, is mixed with water and combined with the activated bauxite.

The preferred process to deactivate the clay impurities and to recondition the adsorbent is as follows: (1) impregnate the activated bauxite adsorbent with a chemical compound from the group consisting of either potassium chloride, sodium chloride, magnesium chloride, lithium chloride, or calcium chloride; (2) Heat treat the impregnated activated bauxite in a muffle furnace at approximately 750 degrees centigrade for 10-15 hrs. allowing the chemical compound to react with the clay minerals; (3) Wash the heat treated impregnated activated bauxite with water to remove the excess chemical compound; (4) Acid-leach the washed impregnated activated bauxite to remove the residual alkalis after the chemical compound is washed with water as described in step 3; (5) Heat treat the impregnated activated bauxite with simulated PFBC exhaust or off-gas, to condition the impregnated activated bauxite; and (6) Process the washed impregnated activated bauxite by Soxhlet-extraction using distilled water to form the regenerable activated bauxite adsorbent Soxhlet-extraction is a wash process whereby in a confined area distilled water is boiled to produce a water vapor. The water vapor is then allowed to condense. The condensate is used to wash and extract any residual alkalis that might contaminate with alkalis found in the PFBC off-gases Soxhlet-extraction of the adsorbent should be continued until no detectable alkalis are present in the extract. By doing this, the regenerable activated bauxite adsorbent is assured of being free from any water soluble alkali. It is also possible to continuously repeat steps 4 and 5 until all of the water-soluble alkali is removed and eliminate step 6.

Now referring to Table 1, tests have shown that the average porosity of fresh activated bauxite to be 38.72%, however, the regenerable activated bauxite impregnated with a chemical compound solution has an average porosity of 42.13%. This impregnation not only opens up the small pores present in the fresh activated bauxite but also creates a substantial number of fine pores causing an increase in the specific surface area, whereby the regenerable activated bauxite has a significant increase in its capacity for the adsorption of alkali vapors.

The alkali-vapor adsorption data of the activated bauxite bed has been mathematically analyzed to provide practical design parameters for the engineering design of the fixed-bed regenerable activated-bauxite adsorber for alkali- vapor concentration detection. The adsorbent bed can be viewed as the sum of two sections, the length of the equilibrium section (LES) and the equivalent length of unused bed (LUB), where $L_0$ is the total length of the adsorber bed, to form the equation :

$$L_0 = LES + LUB.$$

The LES represents the section of the adsorbent bed in which the adsorbate loading of the bed is in the equilibrium with the feed. The adsorbent requirement for this equilibrium section is obtained solely from equilibrium data. The LUB is the additional quantity of adsorbent needed to compensate for the presence of a mass transfer zone (MTZ) during dynamic adsorption. The MTZ is defined as the bed length through which the concentration of the adsorbate is reduced from inlet to outlet conditions. This is derived from the actual test data of the bed length versus the actual alkali loading. The LUB/equilibrium section concept provides a simple and effective method for determination and correlation of rate data. For the design of regenerable activated bauxite probes, LUB is equal to the following:

$$LUB = \tfrac{1}{2} MTZ.$$

Using the LUB/equilibrium section concept, the LES can be calculated from a material balance across the equilibrium section at time $\Theta$:

$$LES = \frac{100G}{\rho_b} \times \frac{\Delta y}{\Delta x} \theta$$

where
G = superficial mass velocity of the feed, g/h-cm$^2$
$\rho_b$ = bulk density of the adsorbent, g/cm$^3$
$\Delta Y$ = change in concentration of adsorbable component in the feed, g/g of feed
$\Delta X$ = delta adsorbate loading, g/100 g of adsorbent
$\Theta$ = time, hrs.

Therefore it is an object of the invention to provide a probe for the detection of alkali vapors in a PFBC exhaust.

It is another object of the invention to provide a regenerable activated bauxite adsorbent that physically adsorbs to the alkalis in the PFBC exhaust to create a water soluble compound.

It is another object of the invention to provide a method of regenerating an adsorbent and providing a probe for reuse in PFBC off-gas.

It is another object of the invention to provide a method of determining the alkali concentration of an off-gas.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form part of the specification, illustrate an embodiment of the present invention and together with the description, serve to explain the principles of the invention. In the drawings:

FIG. 5, shows a second embodiment of the probe including an upper portion comprising the first embodiment of the adsorber; and FIG. 6, shows a third embodiment of the probe including an upper portion comprising the second embodiment of the adsorber.

DETAILED DESCRIPTION OF THE INVENTION

Figures 1, 2:
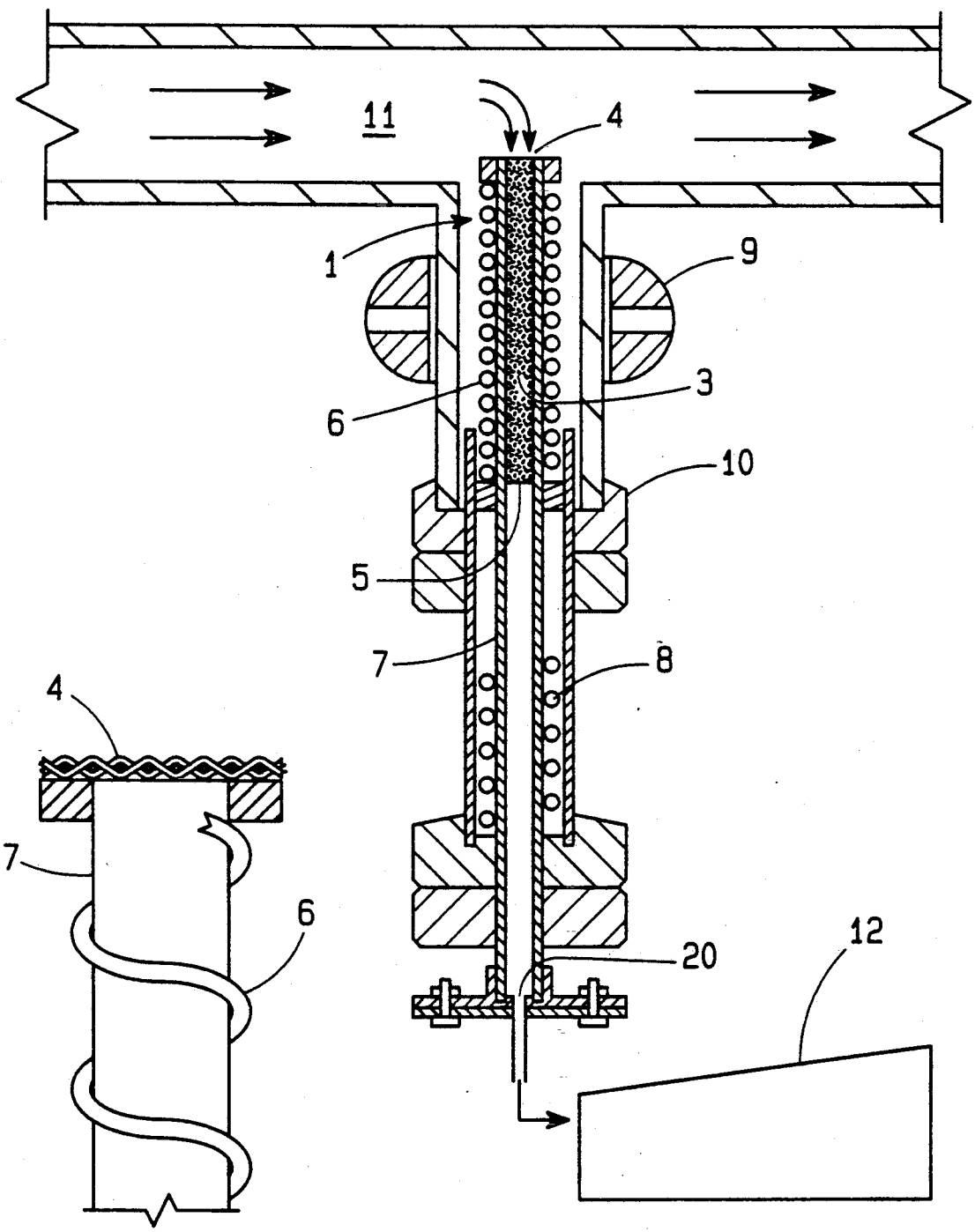
FIG. 1, shows the first embodiment of the probe introduced into a gas stream.
FIG. 2, is a detail of the upper portion of the first embodiment of the probe as shown in FIG. 1.

Referring to FIGS. 1 and 2, the regenerable activated bauxite probe 1 is shown introduced into a gas stream 11 passing through duct 2. It comprises a hollow cylindrical member 7 having a screen mesh at each open end 4, and 5. The hollow cylinder is constructed of either alumina or some other non-alkali reacting material. The regenerable activated bauxite adsorbent 3 is deposed within the hollow cylindrical member 7. A heater coil 6 encircles the hollow cylinder 7 at one end while a cooling coil 8 similarly encircles the other end as indicated in FIG. 1. The coil allows the off-gas to remain at a constant temperature as it travels through the regenerable activated bauxite 3. The cooling coil 8 then cools the probe so that the volume of the sampled gas passes through a flow restricting oriface 20 and flange 10 and is measured by suitable gas volume measuring devices 12.

In operation, the mesh screen 4 allows the entry of the alkali laden gas to enter the probe 7. As the gas passes through the regenerable activated bauxite 3, the alkalis in the gas physically adsorbs to the regenerable activated bauxite 3 to form water soluble compounds. The heater coil 6 heats the gas so that the temperature remains consistent with the temperature of the gas stream 11. As the gas exits through the mesh screen 5 all of the alkali has been removed. The cooling coil 8 then cools the gas and a flow regulating device regulates the gas so that an accurate measurement of the volume of the gas sampled can be determined by the series of instruments 12.

Figures 3, 4:
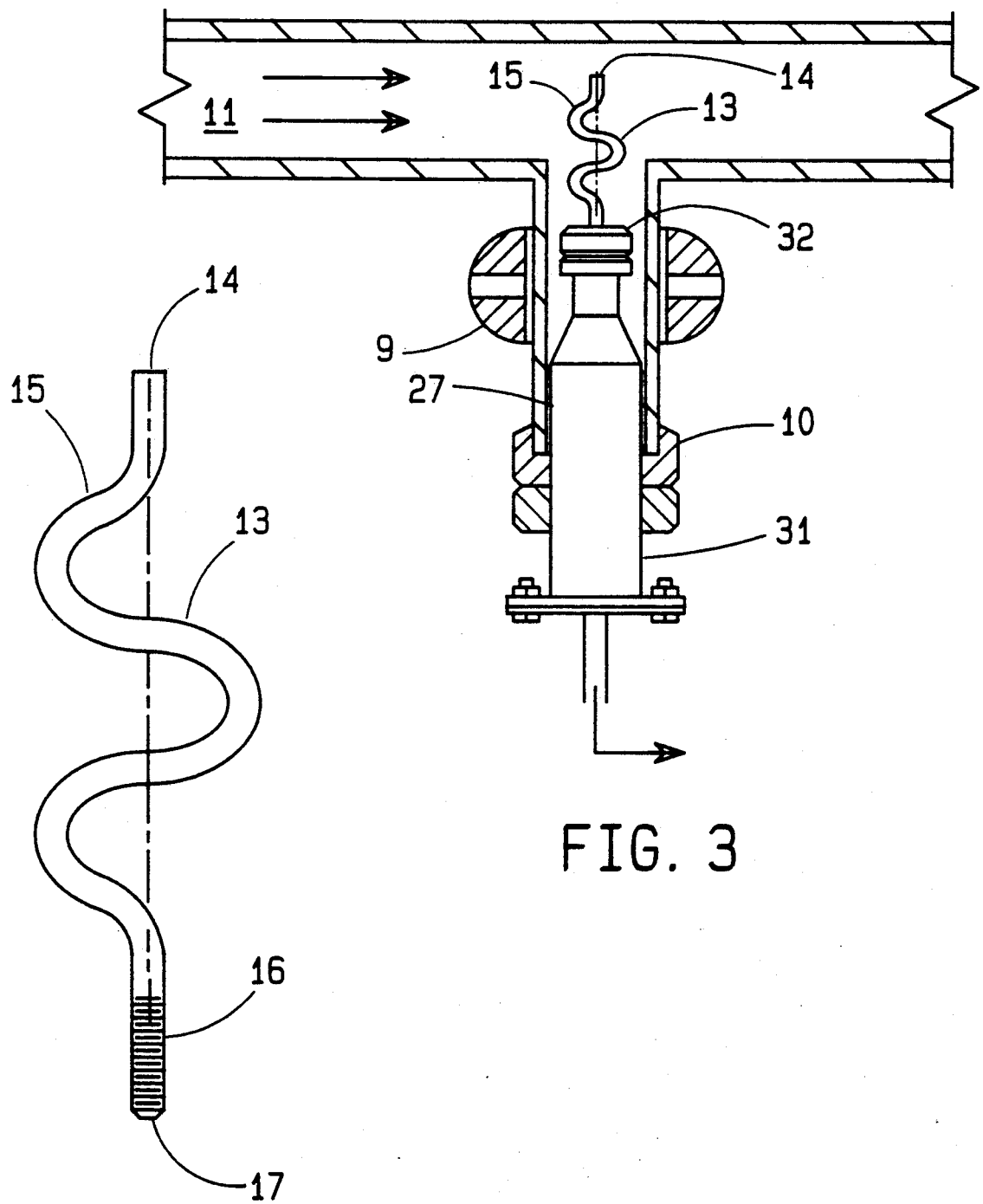
FIG. 3, is a detail of the first embodiment of the adsorber having a spiral configuration.
FIG. 4, is a second embodiment of the adsorber having an internal adsorbent column with a spiral configuration.

FIGS. 3, and 4 show another embodiment of the regenerable activated bauxite adsorber 13 and the probe 31. This adsorber is constructed also of a non-alkali reacting material. The spiral configuration while allowing the same surface area as the first embodiment 7 does not require the heating coil since the spiral configuration compacts the adsorber so that the entire structure is placed within the gas stream. The adsorber 13 has an entry end 14 and an exit end 17 with the exit end being threaded 16. The adsorber 13 can be easily removed by separating the adsorber 13 from the lower portion 27 and by using the method as disclosed the alkali can be removed and extracted and the adsorber replaced. The probe 31 consists of two portions the upper adsorber 13 and the lower portion 27. The upper adsorber 13 is secured to the lower portion by a coupling 32 and the probe 31 is secured in the duct by coupling 10.

FIGS. 5, and 6 shows yet another embodiment of the regenerable activated bauxite adsorber 21, having a spiral chamber 22 in combination with the lower portion 27 to form the probe 33. The regenerable activated bauxite adsorbent 25 is retained by a mesh screen 24. The lower portion of the adsorber being threaded 26 and connected to the lower portion by a coupling 32. Either a flow restrictive oriface 23 or valve can be installed to control the flow of the gases as they pass through the rengenerable activated bauxite adsorbent 25. The lower portion 27 includes a cooling coil 28 and is secured in the duct by a coupling 10.

In the each of the foregoing embodiments, the amount of regenerable activated bauxite adsorbent used is equal to the equation:

$$L_o = LES + LUB$$

$$LES = \frac{100G}{\rho_b} \times \frac{\Delta y}{\Delta x} \theta$$

where
LUB = ½ MTZ = 33.02 cm
G = 492.33 g/h-cm$^2$
$\rho_b$ = 0.88 g/cm$^2$
$\Delta Y$ = 1.49 × 10$^{-6}$ g/g of PFBC process stream
$\Delta X$ = 41.95 × 10$^{-3}$ g/100 -g regenerable activated bauxite
$\Theta$ = time, hrs.

Therefore $L_o$ = 33.02 + 1.99 $\Theta$ and when solving for a sample time with a given probe length of 38.1 cm, $\Theta$ = 2.55 h before an alkali breakout will occur.

The foregoing description of the preferred embodiment of the invention has been presented for purposes of illustration and description. It is not intended to be exhaustive or to limit the invention to the precise form disclosed, and obviously many modifications and variations are possible in light of the above teaching.

TABLE 1

Porosity and Surface Area Measurement for Fresh Activated Bauxite (AB) and NaCl-Treated Regenerable Activated Bauxite (RAB)

| TYPE OF MEASUREMENT | FRESH AB | NaCl-TREATED RAB |
|---|---|---|
| Porosity Measurement | | |
| Total Porosity, % | 38.72 | 42.13 |
| Total Pore Area, m$^2$/g | 58.79 | 66.90 |
| Avg. Pore Diameter, μm | .0180 | .0193 |
| Median Pore Diameter (Volume Basis), μm | .0244 | .1382 |
| Median Pore Diameter (Area Basis), μm | .0083 | .0072 |
| Surface Area Measurement | | |
| N$_2$ BET Specific Surface Area, m$^2$/g | 86.93 | 120.58 |

The embodiments of the invention in which an exclusive property or privelege is claimed are defined as follows:

1. An apparatus for detecting alkali vapors in a gas stream comprising:

a hollow member having a first end opening and a second end opening;

a predetermined quantity of a regenerable activated bauxite adsorbent, wherein said predetermined quantity of said regenerable activated bauxite used is determined by the following equation:

$$L_o = LES + LUB$$

where $$LES = \frac{100G}{\rho_b} \times \frac{\Delta y}{\Delta x} \theta$$

MTZ = mass transfer zone
LUB = ½ MTZ
$L_o$ = predetermined quantity of regenerable activated bauxite
G = superficial mass velocity of the feed, g/h-cm$^2$
$\rho_b$ = bulk density of the adsorbent, g/cm$^3$
$\Delta Y$ = change in concentration of adsorbable component in the feed, g/g of feed
$\Delta X$ = delta adsorbate loading, g/100 g of adsorbent
$\Theta$ = time, hrs, said predetermined quantity of said regenerable activated bauxite deposed in flow through relation within said hollow member and wherein said predetermined quantity of said regenerable activated bauxite adsorbent being selected to detect a pre-established alkali concentration in the gas stream;

means for retaining attached at said first end opening and second end opening of said hollow member and in contact with said regenerable activated bauxite adsorbent; and means for selectively conducting a predetermined quantity of said gas stream through said regenerable activated bauxite adsorbent via said first and second end openings.

2. An apparatus for detecting alkali vapors in a gas stream, as recited in claim 1 comprising:

a means for cooling said gas stream encircling said second end opening of said hollow member.

3. An apparatus for detecting alkali vapors in a gas stream, as recited in claim 2 wherein said regenerable activated bauxite adsorbent is created by the steps of:

(1) impregnating an activated bauxite with a chemical compound, (2) heat treating said impregnated activated bauxite in a furnace to approximately 750 degrees celsius, (3) washing said impregnated activated bauxite with water to remove said chemical compound excess, (4) acid-leaching said impregnated activated bauxite, (5) heat treating said impregnated activated bauxite with a simulated off-gas, and (6) processing said impregnated activated bauxite by Soxhlet-extraction.

4. An apparatus for the detection of alkali vapors in a gas stream as recited in claim 3, wherein said chemical compound comprises:

a compound selected from the group consisting of potassium chloride, sodium chloride, magnesium chloride, lithium chloride, or calcium chloride.

5. An apparatus for the detection of alkali vapors in a gas stream as recited in claim 4, wherein said hollow member comprises:

a non-reacting alumina material.

6. An apparatus for the detection of alkali vapors in a gas stream as recited in claim 4 comprising:

means for heating encircling said hollow member and having the ability to keep said gas stream at a constant temperature as it passes through said regenerable activated bauxite adsorbent.

7. An apparatus for the detection of alkali vapors in a gas stream as recited in claim 4:
wherein said hollow member has a spiral configuration.

8. An apparatus for the detection of alkali vapors in an gas stream as recited in claim 4:
wherein said hollow member has a chamber allowing said regenerable activated bauxite adsorbent to be deposed within said hollow member in a spiral configuration.

9. A method of measuring the alkali concentration of a gas stream comprising the steps of:
(1) introducing a probe containing a predetermined amount of an adsorbent into said gas stream to sample said gas stream for a measured period of time, and wherein said predetermined amount of adsorbent used is determined by the following equation :

$$L_o = LES + LUB$$

where $$LES = \frac{100G}{\rho_b} \times \frac{\Delta y}{\Delta x} \theta$$

MTZ = mass transfer zone
LUB = ½ MTZ
$L_o$ = predetermined quantity of regenerable activated bauxite
G = superficial mass velocity of the feed, g/h-cm$^2$
$\rho_b$ = bulk density of the adsorbent, g/cm$^3$
$\Delta Y$ = change in concentration of adsorbable component in the feed, g/g of feed
$\Delta X$ = delta adsorbate loading, g/100 g of adsorbent
$\theta$ = time, hrs, (2) capturing said alkalis with said adsorbent;
(3) water leaching said adsorbent to release said captured alkalis;
(4) determining the volume of said gas stream sampled; and
(5) determining said alkali concentration by using said captured alkalis and said volume of said gas stream.

10. A method of measuring the alkali concentration of a gas stream, as recited in claim 9, wherein said probe comprises:
a hollow member having a top end and a bottom end;
a predetermined quantity of a regenerable activated bauxite adsorbent deposed in said hollow member; and
means for retaining attached at said top end and bottom end of said hollow member and in contact with said regenerable activated bauxite adsorbent, having the ability to allow said gas stream to pass through said top end of said hollow member and exit at said bottom end while retaining said regenerable activated bauxite adsorber.

11. A method of measuring the alkali content of a gas, stream as recited in claim 10, wherein said probe comprises:
a regenerable activated bauxite adsorbent created by the steps of (1) impregnating an activated bauxite with a chemical compound, (2) heat treating said impregnated activated bauxite in a furnace to approximately 750 degrees celsius, (3) washing said impregnated activated bauxite with water to remove said chemical compound excess, (4) acid-leaching said impregnated activated bauxite, (5) heat treating said impregnated activated bauxite with a simulated off-gas, and (6) processing said impregnated activated bauxite by Soxhlet-extraction.

12. A method of measuring the alkali content of a gas stream, as recited in claim 10 wherein said chemical compound comprises:
a compound selected from the group consisting of potassium chloride, sodium chloride, magnesium chloride, lithium chloride, or calcium chloride.

13. A method of measuring the alkali content of a gas stream, as recited in claim 11, wherein said hollow member comprises:
a spiral configuration.

14. A method of measuring the alkali content of a gas stream, as recited in claim 11:
wherein said hollow member has a chamber allowing said regenerable activated bauxite adsorbent to be deposed within said hollow member in a spiral configuration.

* * * * *